United States Patent

Woskov et al.

[11] Patent Number: 5,909,277
[45] Date of Patent: Jun. 1, 1999

[54] MICROWAVE PLASMA ELEMENT SENSOR

[75] Inventors: Paul Woskov, Bedford; Kamal Hadidi, Cambridge; Paul Thomas, Natick, all of Mass.

[73] Assignee: Massachusetts Institute of Technology, Cambridge, Mass.

[21] Appl. No.: 09/040,190

[22] Filed: Feb. 13, 1998

[51] Int. Cl.$^6$ .................................................. G01N 21/73
[52] U.S. Cl. ............................................................ 356/316
[58] Field of Search ........................... 356/316; 250/288, 250/252.1

[56] References Cited

U.S. PATENT DOCUMENTS 5,252,827  10/1993  Koga et al. ........................... 250/252.1
5,479,254  12/1995  Woskov et al. .
5,671,045   9/1997  Woskov et al. .

*Primary Examiner*—F. L. Evans
*Attorney, Agent, or Firm*—Choate, Hall & Stewart

[57] ABSTRACT

The apparatus for analyzing a sample gas includes a source of microwave energy directed onto the sample gas to create a plasma. A spectrometer is arranged to receive light from the plasma to identify different elements and/or to determine the concentration of at least one element in the sample gas. In one embodiment, an attached calibration system is provided for calibrating the output of the spectrometer. The calibration system includes a nebulizer apparatus for introducing a controlled amount of at least one element into the sample gas. The apparatus also includes structure adapted to add a swirl component to the plasma gas flow as an aid to plasma confinement. It is also preferred that a pair of electrodes contacting the sample gas be provided for igniting the plasma.

8 Claims, 4 Drawing Sheets

MICROWAVE PLASMA ELEMENT SENSOR

BACKGROUND OF THE INVENTION

This invention relates to method and apparatus for analyzing elemental composition in a gas stream, and more particularly to method and apparatus for continuous, real time element monitoring using a microwave-induced plasma and atomic emission spectroscopy.

U.S. Pat. Nos. 5,479,254 and 5,671,045 are directed to microwave-induced plasma systems for continuous, real-time element monitoring. The method and apparatus disclosed and claimed in these two patents have application in detecting elements in exhaust gases from all types of furnaces. Furnaces often emit hazardous metals such as chromium, lead and beryllium. The monitoring of off-gas emissions is important in preventing environmental pollution by making it possible to insure that such processes meet environmental regulations.

The present invention is an improvement on the highly effective technology in U.S. Pat. Nos. 5,479,254 and 5,671,045, the teachings of which are incorporated in their entirety herein.

SUMMARY OF THE INVENTION

In one aspect, the apparatus for analyzing a sample gas includes a source of microwave energy directed upon the sample gas to create a plasma. A spectrometer is arranged to receive light from the plasma to determine the concentration of at least one element in the sample gas. A calibration system is provided for calibrating the output of the spectrometer and this calibration system includes nebulizer apparatus for introducing a controlled amount of the at least one element into the sample gas. In one embodiment, apparatus is included to swirl the sample gas as an aid to confinement. In yet another embodiment, a pair of electrodes is provided for contacting the sample gas for igniting the plasma. A starter circuit is provided for energizing the pair of electrodes. In another aspect, the spectrometer identifies an element or elements in the sample gas without necessarily determining the concentration.

In yet another aspect, the apparatus of the invention includes an enclosure through which the sample gas flows, a portion of the enclosure forming a swirl chamber causing a rotating gas layer between the axially introduced sample gas and the chamber wall. The rotation keeps the plasma from attaching to the wall and more reliably centered. A pair of electrodes is disposed within the enclosure forming part of a high voltage igniter circuit to ignite the plasma. A waveguide directs microwaves into the enclosure for sustaining the plasma and a spectrometer is arranged to receive light from the plasma. A calibration system introduces a known quantity of an element into the gas for calibrating the sensor.

The improved apparatus of the invention makes it possible to more reliably start the plasma, to keep the plasma more reliably centered inside the device with longer life time between failures and to make possible accurate metal concentration measurements.

BRIEF DESCRIPTION OF THE DRAWINGS

A more complete understanding of the invention may be attained by reference to the drawings, in which.

DESCRIPTION OF THE PREFERRED EMBODIMENT

Figure 1:
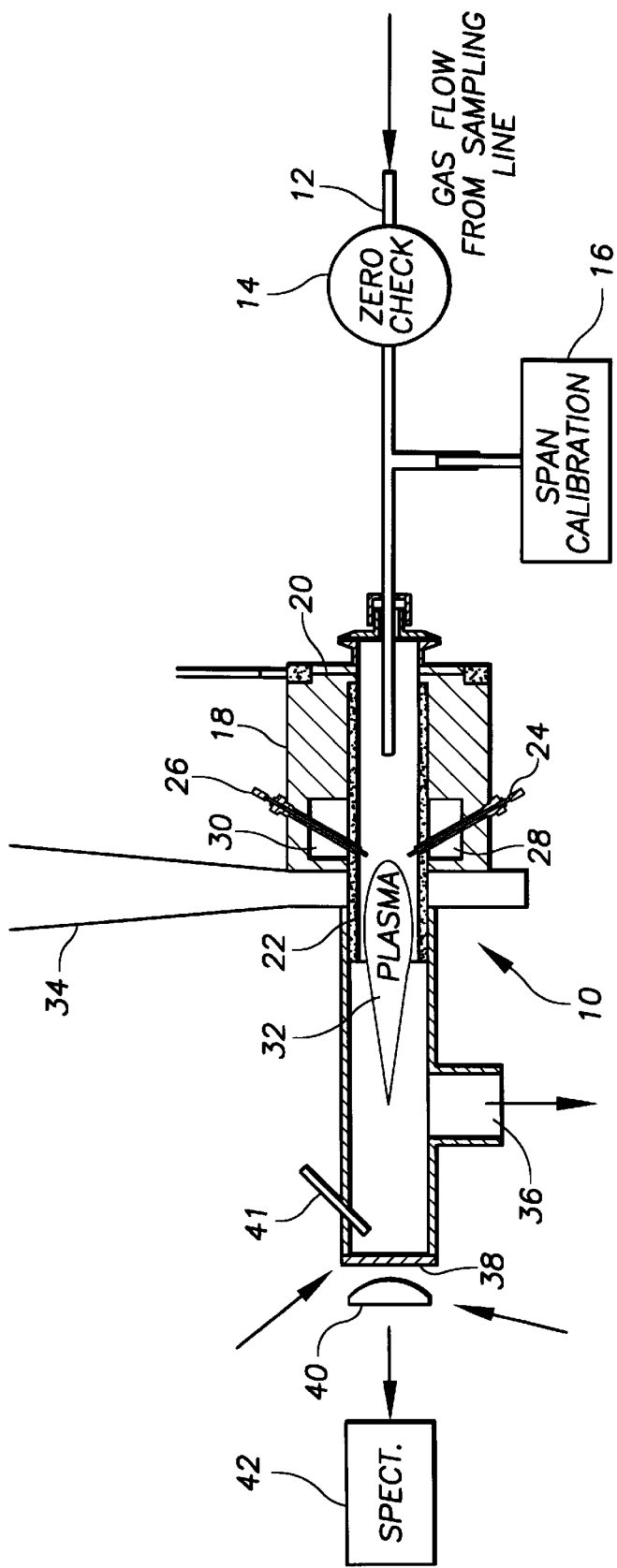
FIG. 1 is a cross-sectional view of the microwave-plasma element monitor of the invention.

With reference to FIG. 1, an element monitor 10 of the invention includes a sample tube 12 into which gas including an element or elements to be monitored is introduced from, for example, a furnace (not shown) whose off-gases are to be monitored. Gas flows through a zero check section 14 and a span calibration section 16.

The zero check section 14 and span calibration section 16 form a calibration system which will be described below in conjunction with FIG. 4. The sample gas then enters an enclosure 18 which includes a swirl chamber 20 which will be described in more detail below in conjunction with FIG. 3. A dielectric tube 22 forms an interior portion of the enclosure 18. Starter electrodes 24 and 26 extend into the interior of the dielectric tube 22 and are mounted within recesses 28 and 30 in the enclosure 18. The starter electrodes 24 and 26 initiate a plasma 32 which is sustained by microwave energy in a waveguide 34. The sample gas is removed through an exhaust 36. Light from the plasma 32 passes through a window 38 and is collected by light collection optics 40 and enters a spectrometer 42. A window cleaning gas jet 44 may be provided to clean the window 38.

Figure 2:
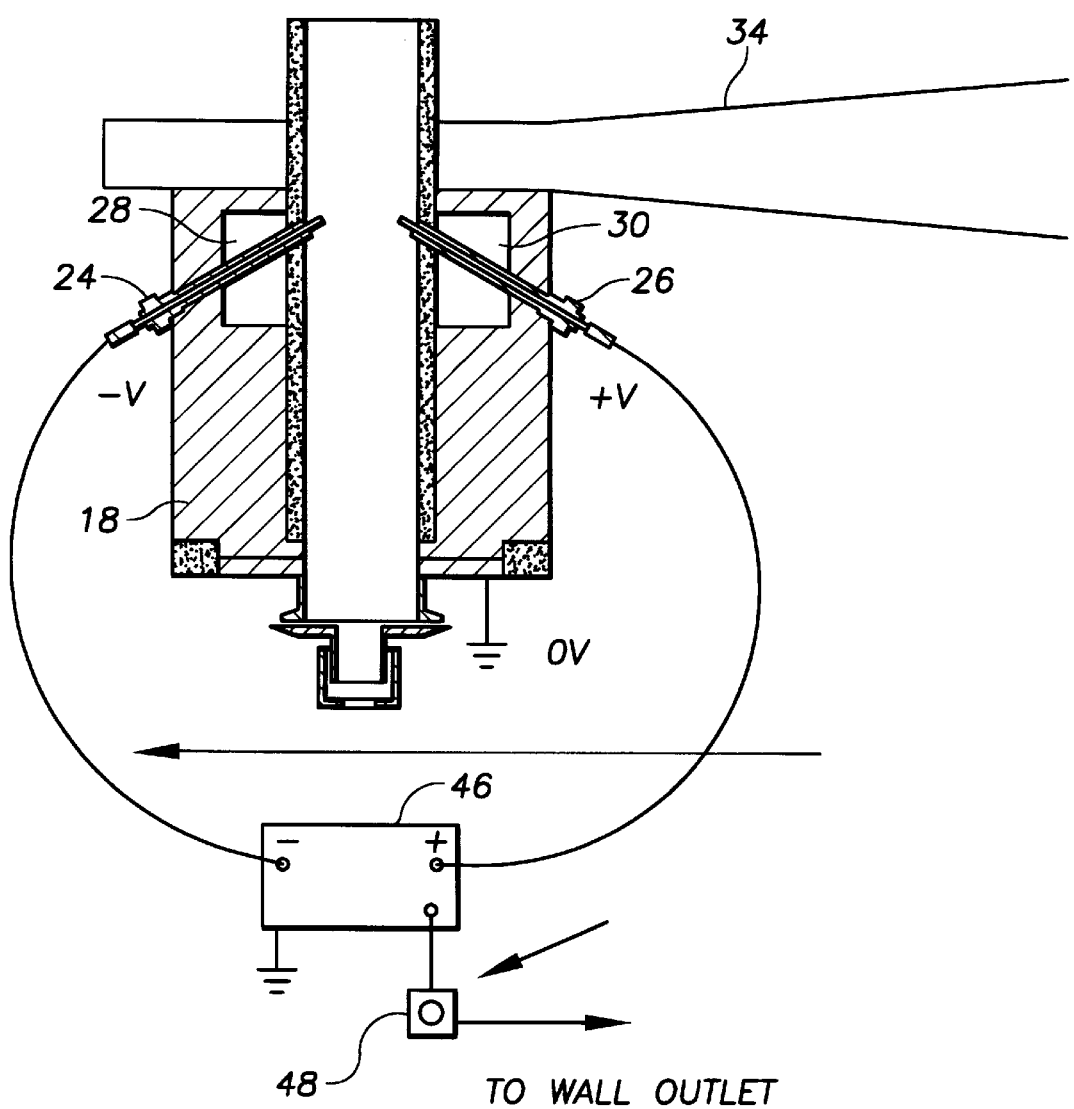
FIG. 2 is the dual electrode starter circuit used in conjunction with the embodiment of FIG. 1.

With reference now to FIGS. 1 and 2, the microwave-plasma starter electrodes 24 and 26 create the initial electric spark which the microwave-power then enlarges and sustains as a continuous plasma. The starter system disclosed herein is powered by a high-voltage power supply 46 which is connected to the electrodes 24 and 26. The voltage difference between the electrodes 24 and 26 is twice the voltage difference between any one electrode and the enclosure 18. Typically, the enclosure 18 potential is grounded (zero volts) and one electrode will be positive by half the starter voltage difference and the other electrode will be negative by half the voltage difference. This arrangement makes it possible to have a larger spark inside the device structure without arcing to the device walls. Furthermore, the spark electrodes 24 and 26 are made adjustable so that their relative separation and/or positioning to the waveguide can be optimized for plasma starting and then after starting they can be retracted to minimize microwave power leakage. The starter electrodes 24 and 26 in this embodiment are solid tungsten wire and are enclosed inside high-voltage insulating alumina sleeves with the ends of the wire protruding from the insulation. The electrodes are inserted into the enclosure 18 through air tight feedthroughs into the gas flow just up stream of the waveguide 34. The inner walls through which these electrodes are inserted are recessed (28 and 30) to further minimize the possibility of arcing to the walls. In the embodiment shown, the electrodes are inserted at an angle relative to the gas flow direction so that when they are pushed in to decrease the gap between them they also move closer to the waveguide. Other angular orientations for the electrodes are possible.

Electrical connectors attached to the outside end of the electrodes 24 and 26 connect high voltage wires from the high voltage power supply 46. One lead is negative relative to ground by a voltage, V, and the other is positive by voltage, V, so that the difference between the electrodes is 2 V. The body of the microwave-plasma device is grounded to 0 V. The power supply 46 is connected to a power line through a momentary contact switch 48 which when closed energizes the power supply 46. In tests performed at the Massachusetts Institute of Technology, a high voltage step up transformer was used as the starter power supply which stepped up the wall outlet line voltage from 120 volts to ±7500 volts for a voltage difference of 15,000 volts between the electrodes 24 and 26. The momentary switch is generally closed for one to two seconds to start the plasma.

Figure 3:
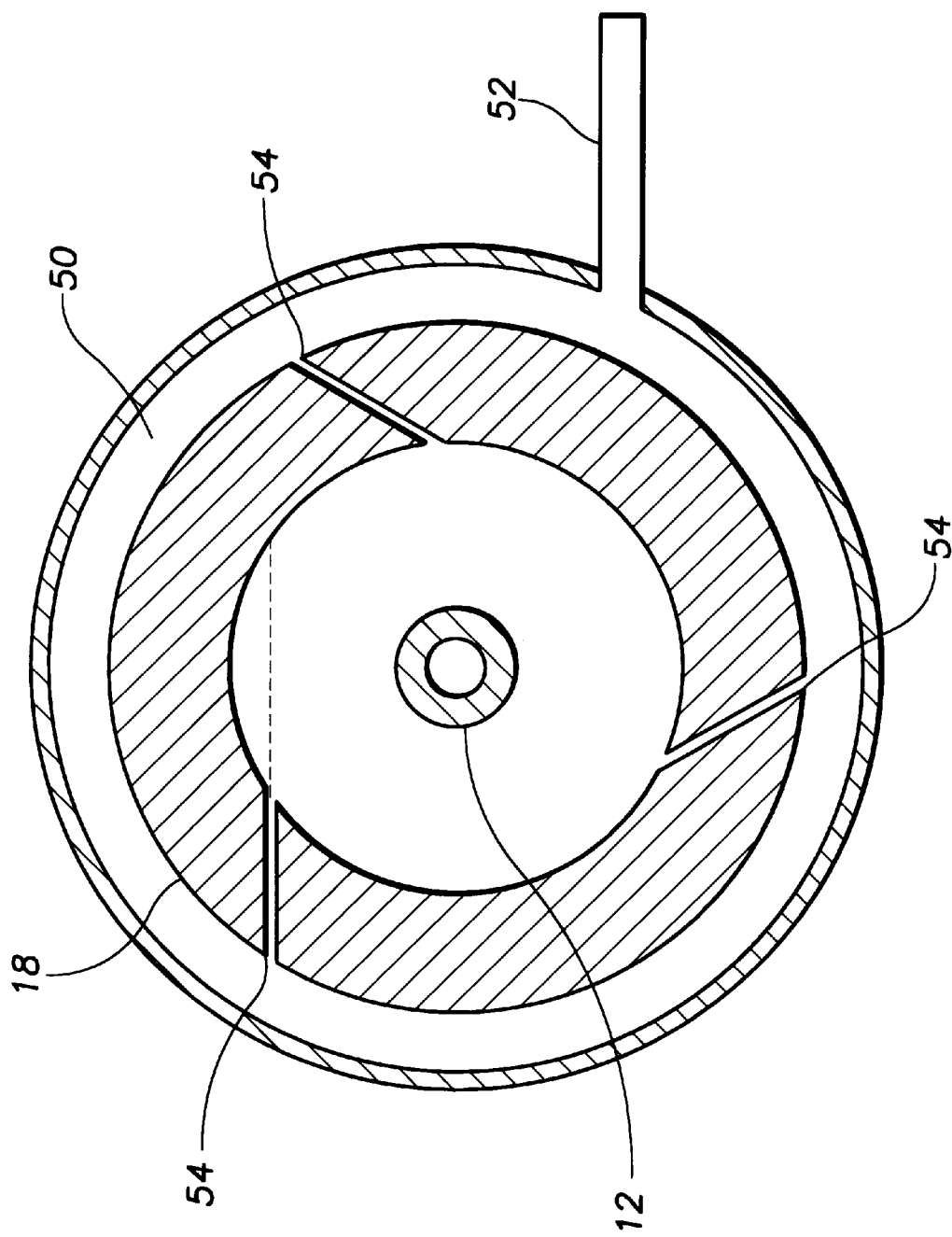
FIG. 3 is a cross-sectional view of the swirl chamber forming a part of the apparatus.

A swirling gas flow along the inner wall of the plasma enclosure 18 is used to center the plasma 32 inside the dielectric tube 22 to prevent plasma contact with the walls. With reference to FIGS. 1 and 3, the swirl gas flow system is located at the base of the input side of the enclosure 18, concentric around the sample tube 12. A cross section of the structure of the swirl gas system in a plane perpendicular to the plane of FIG. 1 is shown in FIG. 3. An annular swirl chamber 50 encircles the plasma chamber enclosure 18. The swirl chamber 50 is connected to an external supply of pressurized gas through a connection 52. The external gas may be air, nitrogen, or some other gas with which the plasma 32 performs well for atomic emission spectroscopy. Small diameter swirl jet holes 54 are machined through the wall separating the swirl chamber 50 from the interior of the enclosure 18. The swirl jet holes 54 are directed tangentially to the circumference of the inner wall of the plasma chamber. The tangent is offset from the wall as shown to more efficiently establish a swirling gas flow. The diameter of the swirl jets should be kept as small as possible to minimize the volume of swirl gas flow and maximize swirl gas flow velocity. Tests have shown that the swirl gas volume needs to be less than or equal to the sample gas flow volume to prevent significant degradation of the sensitivity of the microwave-plasma monitor 10 to trace elements in the sample gas flow. It should be noted that the swirl gas not only helps to confine the plasma but may be tailored in composition to heighten sensitivity to particular metals. Tests have shown that helium helps detect the element mercury.

In U.S. Pat. Nos. 5,479,254 and 5,671,045 referred to earlier, the plasma centering function was performed by an axially positioned dielectric rod or small tube inserted all the way to the base of the plasma frame. The tube acted as a thermal electron emitter in contact with the plasma so as to keep it centered. Experience with this design has taught that the central electron emitter rod/tube breaks often due to thermal stresses, thereby requiring frequent replacement. The reliability of the microwave-plasma hardware is significantly improved by recessing any axially positioned dielectric tubes such as the sample tube 12 well away from the plasma flame and utilizing a swirling gas flow to confine the plasma to the center of the plasma chamber.

An important part of the present invention is the calibration system including the zero check section 14 and the span calibration section 16. These elements are shown in FIG. 4. An attached calibration system is necessary to insure instrument measurement accuracy of element concentrations in the sampled gas flow. Such a system makes possible the verification of measurement accuracy whenever and as often as necessary to maintain confidence in the measurements. Attachment of the calibration system at the gas flow input to the plasma device allows calibration for variable sample gas compositions as well as for all other possible changes to the instrument over time which affect sensitivity, such as degradation of light collection optics due to window 38 depositions or misalignment and drifts in the light detection electronics.

The calibration system consists of two parts. One part is a zero check of the plasma light emission level when there are no particulates or monitored elements in the sampled gas, which otherwise is of the same chemistry and the same flow velocity. The other part is a span calibration which injects a known concentration of an element or elements being monitored to determine the signal response for that concentration. The span calibration concentration is chosen to be within the linear instrument response of the unknown concentration being monitored. The monitored sample composition is simply the signal level above zero times the span calibration concentration divided by the span signal above zero.

Figure 4:
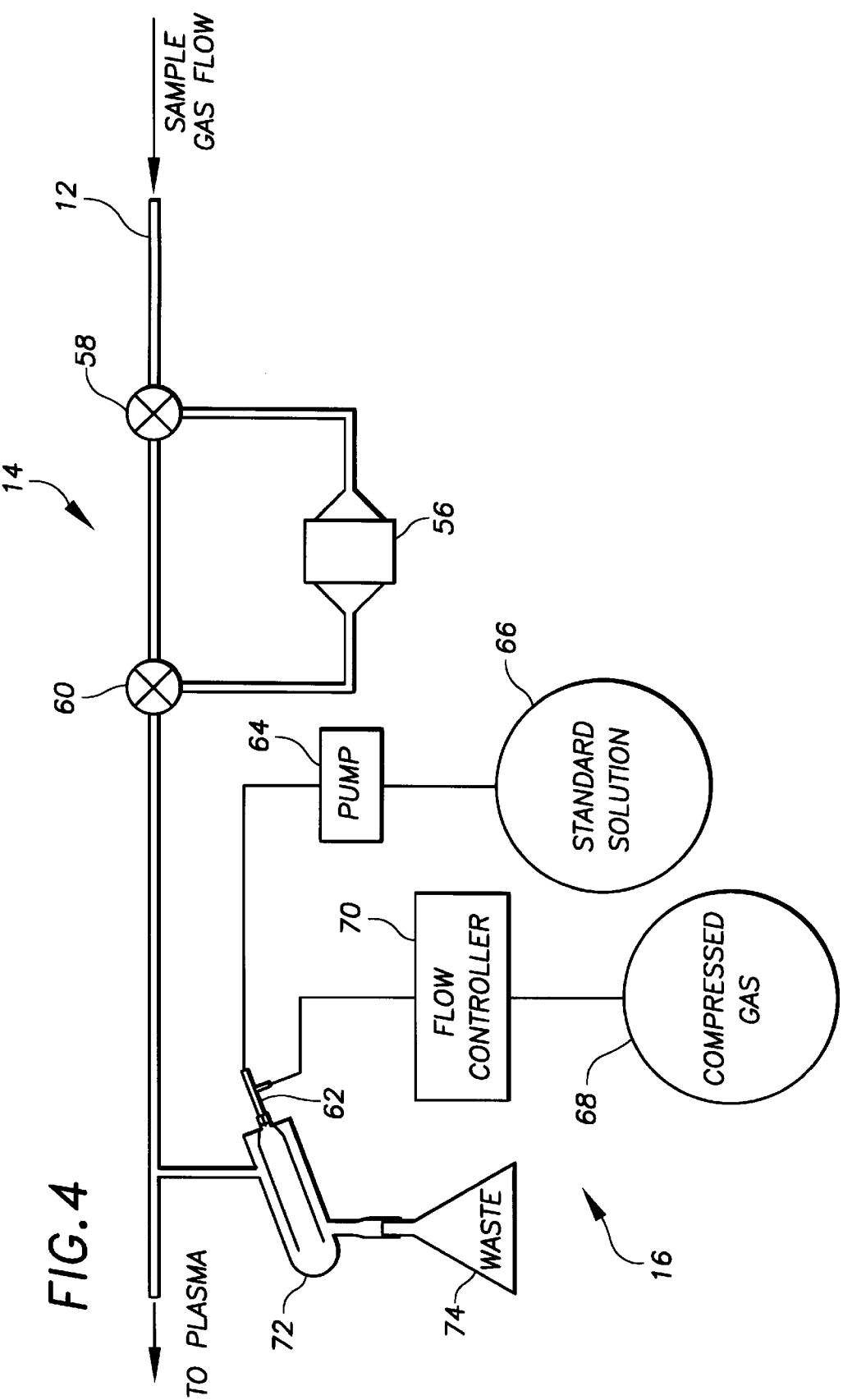
FIG. 4 is a schematic illustration of the calibration system used in the invention.

As shown in FIG. 4, the zero check section 14 includes a filter 56 connected into the sample line 12 by valves 58 and 60. Sample gas flow is intermittently diverted through the filter 56 which removes particulates and vapors of elements being monitored. The filter 56 may be a combination of a fine particulate filter and activated carbon for heavy metals monitoring. The sample gas line 12 cross section is expanded at the filter to overcome gas flow resistance to maintain the gas flow velocity as near as possible to the unfiltered velocity. The sample line 12 and the filter 56 may also be heated to maintain identical conditions through the two gas flow routes. The two valves 58 and 60 in the sample line 12 are controlled in synchronism and intermittently divert the sample line through the filter whenever a zero check is needed.

The span calibration section 16 includes a liquid nebulizer 62 to create an aerosol containing a known quantity of the elements being monitored which then become entrained in the sample gas flow. Either a pneumatic nebulizer or a more efficient ultrasonic nebulizer may be used. The liquid input to the nebulizer is supplied by a pump 64 which delivers, at constant pressure, a standard solution 66 of a known concentration of elements. Compressed gas 68 to the pneumatic nebulizer 62 is supplied through a flow controller 70 to maintain an accurately metered aerosol generation of the standard solution 66. The compressed gas 68 may be air, nitrogen, helium, or other medium which is compatible with the microwave-plasma operation for sensitive detection.

A spray chamber 72 is used with the pneumatic nebulizer 62 to filter out large liquid droplets from the aerosol. The filtered liquid droplets are collected in a waste receptacle 74 which is connected to the spray chamber 72 by an air tight seal. An air tight seal is necessary because the sample line could be part of the vacuum system of the monitored process.

With reference again to FIG. 1, it is noted that viewing an analytical plasma along its axial direction for atomic emission spectroscopy is not by itself a new development. See, for example, "Axial ICP Analysis", page 2, Leeman Letter, No. 37, September 1995.

However, axial viewing in the microwave-plasma element monitor of the invention is novel. In the arrangement of FIG. 1, the system is designed with the exhaust 36 exiting sideways to the axis of the plasma 32 along the gas flow through the waveguide 34. This arrangement provides a clear line of sight for the light emission to be viewed axially. The window 38 seals the plasma chamber downstream of the plasma 32. The window 38 material is preferably fused quartz so that it is transparent to ultraviolet light. The gas jet 44 directed at the inside of window 38 keeps it clean. Light collection optics 40, such as a lens and fiber optics, view the plasma through the window 38 and transmit the light to the spectrometer 42 for detection and analysis.

In operation, the system is initially calibrated by setting the valves 58 and 60 to cause the sample gas to flow through the filter 56 before entering the enclosure 18. The spectrometer 42 will then give a zero element reading to establish a baseline. Thereafter, the span calibration portion 16 injects a known amount of an element into the sample tube 12 and the spectrometer 42 produces a signal in response to the known amount of the known injected element. The system is now calibrated for element identity and concentration and the sample gas flows directly into the enclosure 18 where the plasma 32 is sustained by microwave energy in the waveguide 34. Light from the plasma 32 is detected by the spectrometer 42 which produces a signal from which the concentration of a monitored element may be determined based upon the earlier calibration.

It is intended that all modifications and variations of the present invention be included within the scope of the appended claims.

What is claimed is:

1. Apparatus for analyzing a sample gas comprising:
    a source of microwave energy directed upon the sample gas to create a plasma;
    a spectrometer arranged to receive light from the plasma to determine the concentration of at least one element in the sample gas; and
    a calibration system for calibrating the output of the spectrometer, the calibration system comprising nebulizer apparatus for introducing a controlled amount of the at least one element into the sample gas.

2. Apparatus for analyzing a sample gas comprising:
    a source of microwave energy directed upon the sample gas to create a plasma;
    a spectrometer arranged to receive light from the plasma to determine the concentration of at least one element in the sample gas; and
    apparatus adapted to add a swirl component to the plasma gas flow as an aid to plasma confinement.

3. Apparatus for analyzing a sample gas comprising:
    a source of microwave energy directed upon the sample gas to create a plasma;
    a spectrometer arranged to receive light from the plasma to determine the concentration of at least one element in the sample gas; and
    a pair of electrodes contacting the sample gas for igniting the plasma.

4. The apparatus of claim 3 further including power supply means for generating a voltage of approximately 15,000 volts between the pair of electrodes.

5. Apparatus for analyzing the composition of a sample gas comprising:
    an enclosure through which the sample gas flows, a portion of the enclosure forming a swirl chamber causing at least a portion of the plasma gas to rotate;
    a pair of electrodes disposed within the enclosure, the electrodes forming part of a high voltage ignitor circuit to ignite a plasma;
    a waveguide for directing microwaves into the enclosure for sustaining the plasma;
    a spectrometer arranged to receive light from the plasma; and
    a calibration system for introducing a known quantity of an element into the gas.

6. The apparatus of claim 5 wherein the calibration system includes a nebulizer.

7. Apparatus for analyzing a gas sample comprising:
    a source of microwave energy directed upon the sample gas to create a plasma;
    a spectrometer arranged to receive light from the plasma to identify at least one element in the sample gas; and
    apparatus adapted to add a swirl component to the plasma gas flow as an aid to plasma confinement.

8. Apparatus for analyzing a sample gas comprising:
    a source of microwave energy directed upon the sample gas to create a plasma;
    a spectrometer arranged to receive light from the plasma to identify at least one element in the sample gas; and
    a pair of electrodes contacting the sample gas for igniting the plasma.

* * * * *

UNITED STATES PATENT AND TRADEMARK OFFICE
CERTIFICATE OF CORRECTION

PATENT NO. : 5,909,277

DATED : June 1, 1999

INVENTOR(S) : Paul Woskov, et al.

It is certified that error appears in the above-identified patent and that said Letters Patent is hereby corrected as shown below:

Column 1, under the title, insert

--This invention was made with government support under Grant number DE-FG02-94ER54235 awarded by the U.S. Department of Energy. The government has certain rights in the invention.--.

Signed and Sealed this

Thirtieth Day of November, 1999

Attest:

Q. TODD DICKINSON

*Attesting Officer*   *Acting Commissioner of Patents and Trademarks*